United States Patent [19]
Desmurs et al.

[11] Patent Number: 5,637,773
[45] Date of Patent: Jun. 10, 1997

[54] ACYLATION OF AROMATIC ETHERS/ PHENOLS

[75] Inventors: Jean-Roger Desmurs, St-Symphorien D'Ozon; Jacques Dubac, Pechbusque; Mireille Labrouillere, Agen; André Laporterie, Pompertuzat, all of France

[73] Assignee: Rhone-Poulenc Chimie, Courbevoie Cedex, France

[21] Appl. No.: 518,810

[22] Filed: Aug. 24, 1995

[30] Foreign Application Priority Data

Aug. 24, 1994 [FR] France ................... 94 10253

[51] Int. Cl.$^6$ ................................... C07C 45/46
[52] U.S. Cl. ........................... 568/319; 568/322
[58] Field of Search ................. 568/319, 322, 568/323

[56] References Cited

U.S. PATENT DOCUMENTS 4,960,943 10/1990 Botta et al. ................. 568/322

FOREIGN PATENT DOCUMENTS 0067698 12/1982 European Pat. Off. .
0600318 6/1994 European Pat. Off. .

OTHER PUBLICATIONS

Dermer et al, JACS, vol. 64, pp. 464–465 (1942).

Dermer et al (II), J.A.C.S; vol. 63, pp. 2881–2883 (1941).

Primary Examiner—James H. Reamer
Attorney, Agent, or Firm—Burns, Doane, Swecker & Mathis, L.L.P.

[57] ABSTRACT

Aromatic ethers/phenols are acylated, characteristically into hydroxy- and/or alkoxyaromatic alkylketones, and in particular, are acylated in the para-position relative to an alkoxy substituent borne by the aromatic nucleus, by reacting/condensing same with an acylation agent, for example acetyl chloride or acetic anhydride, in the presence of a catalytically effective amount of a bismuth halide, or a precursor compound that generates, in situ, a bismuth halide.

22 Claims, No Drawings

ACYLATION OF AROMATIC ETHERS/PHENOLS

BACKGROUND OF THE INVENTION

1. Technical Field of the Invention

The present invention relates to the acylation of aromatic ethers or phenols, and, more especially, to the acylation of aromatic ethers in the para-position relative to an alkoxy radical borne by the aromatic ring nucleus.

In a preferred embodiment of the invention, acetyl chloride or acetic anhydride is condensed with an aromatic ether to prepare an alkoxyaromatic alkylketone.

2. Description of the Prior Art

A conventional process for the preparation of aromatic ketones is via a Friedel-Crafts type acylation reaction.

The aromatic compound is reacted with an acylation or acylating agent in the presence of a catalyst, generally aluminum chloride.

Compare Kuroda et al, *Sci. Papers Inst. Phys. Chem. Res.*, 18, pp 51–60 (1932), which describes the preparation of methoxyacetophenones by reacting an aromatic compound substituted by 1 to 3 methoxy groups with acetyl chloride in the presence of aluminum chloride.

The use of aluminum chloride, however, presents a number of drawbacks. Aluminum chloride is corrosive and an irritant. In addition, aluminum chloride must be used in large amounts, at least equal to the stoichiometric amount, due to complexation of the ketone formed. As a consequence, aluminum chloride is not a true catalyst.

At the end of the reaction, the aluminum chloride must be removed from the reaction medium via acidic or basic hydrolysis.

Such hydrolysis technique requires the addition of water to the reaction medium, considerably complicating the process, since the metallic cation, in particular the aluminum cation, forms polyoxo- and/or polyhydroxo-aluminum complexes of a milky consistency in the presence of water, and are difficult to separate. A lengthy and expensive treatment, thus, has to be carried out after hydrolysis, comprising extraction of the organic phase, separation of the aqueous and organic phases, and even drying of the latter. Hence, separation of the aluminum chloride is a long and expensive process.

Further, there is the problem with the aqueous saline effluents, which must be neutralized, mandating a supplemental operation.

Still further, the aluminum chloride cannot be recycled, since it has been hydrolyzed.

To overcome this problem, Atsushi Kawada et al, *J. Chem. Soc. Chem. Commun.*, p 1158 (1993), describe carrying out the acylation of an aromatic compound by means of acetic anhydride, in the presence of a catalytic amount of a trifluoromethane sulfonate of a lanthanide, in particular ytterbium. However, the catalyst is expensive and difficult to synthesize.

SUMMARY OF THE INVENTION

Accordingly, a major object of the present invention is the provision of an improved process for the acylation of aromatic ethers and phenols, characteristically into hydroxy- and/or alkoxyaromatic alkylketones, and which novel process avoids or conspicuously ameliorates the above disadvantages and drawbacks to date characterizing the state of this art.

Briefly, the present invention features a process for the acylation of an aromatic ether or phenol which comprises reacting such aromatic compound with an acylation agent, in the presence of a catalyst, then recovering the product formed, and wherein the acylation reaction is carried out in the presence of a catalytically effective amount of a bismuth halide, or any precursor compound which generates the bismuth halide in situ.

DETAILED DESCRIPTION OF BEST MODE AND PREFERRED EMBODIMENTS OF THE INVENTION

More particularly according to the present invention, by the term "aromatic ether or phenol" is intended an aromatic compound in which a hydrogen atom directly bonded to the aromatic ring is replaced by a hydroxy group or an ether group, and by the term "aromatic compound" is intended the conventional concept of aromaticity as defined in the literature, in particular by Jerry March, *Advanced Organic Chemistry*, 4th edition, pp 40 ff, John Wiley & Sons (1992).

In a preferred embodiment, the present invention features a process for the acylation of an aromatic compound having the general formula (I):

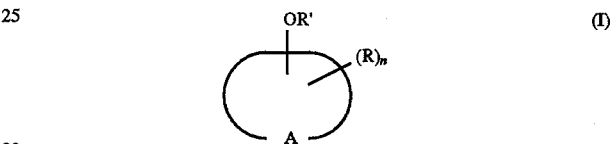

wherein A is the residue or remainder of an optionally substituted cyclic ring member forming or defining all or a fraction of a monocyclic or polycyclic carboxylic aromatic nucleus containing at least one OR' substituent; R is one or more inert substituents, which may be identical or different; R' is a hydrogen atom or hydrocarbon radical having from 1 to 24 carbon atoms, which can be a linear or branched, saturated or unsaturated acyclic aliphatic radical, a monocyclic or polycyclic, saturated, unsaturated or aromatic cycloaliphatic radical, or a linear or branched, saturated or unsaturated aliphatic radical bearing a cyclic substituent; and n is a number less than or equal to 4.

By the term "alkoxy groups" are intended, for simplification, R'—O type radicals in which R' is as defined above. R' thus represents both a saturated, unsaturated or aromatic, aliphatic, acyclic or cycloaliphatic radical, and a saturated or unsaturated aliphatic radical bearing a cyclic substituent.

The aromatic compound employed in the process of the invention advantageously has the formula (I) in which R' is a linear or branched, saturated or unsaturated acyclic aliphatic radical.

More preferably, R' is a linear or branched alkyl radical having from 1 to 12 carbon atoms, preferably 1 to 6 carbon atoms; the hydrocarbon chain or backbone may be interrupted by a heteroatom (oxygen, for example), by a functional group (—CO—, for example) and/or may be substituted (by a halide, for example).

The linear or branched, saturated or unsaturated acyclic aliphatic radical may bear a cyclic substituent. By the term "cycle" is preferably intended a saturated, unsaturated or aromatic cyclic ring member, preferably cycloaliphatic or aromatic, in particular cycloaliphatic having 6 carbon atoms in the cycle, or benzenic.

The acyclic aliphatic radical can be bonded to the cycle by a valence bond, a heteroatom or a functional group, examples of which are given below.

The cycle may be substituted. Examples of cyclic substituents are substituents such as R, the definition of which is given below in respect of formula (Ia).

R' can also be a saturated carbocyclic radical or a carbocyclic radical containing 1 or 2 sites of unsaturation in the ring member, generally having 3 to 7 carbon atoms and preferably 6 carbon atoms in the cycle; the cycle may be substituted by substituents such as R.

R' can also be an aromatic carbocyclic radical, preferably a monocyclic radical generally having at least 4 carbon atoms and preferably 6 carbon atoms in the cycle; the cycle may be substituted by substituents such as R.

The process of the invention is particularly applicable to aromatic compounds of formula (I) wherein R' is a linear or branched alkyl radical having from 1 to 4 carbon atoms, or a phenyl radical.

Exemplary preferred radicals R' include methyl, ethyl, propyl, isopropyl, butyl, isobutyl, sec-butyl, tert-butyl or phenyl radicals.

In formula (I) circumscribing the preferred aromatic compounds, remainder or residue A is advantageously the remainder or residue of a monocyclic aromatic carbocyclic compound having at least 4 carbon atoms, preferably 6 carbon atoms, or the remainder or residue of a polycyclic carbocyclic compound which can be constituted by at least two aromatic carbocycles which together form ortho- or ortho- and pericondensed ring systems, or by at least two carbocycles of which at least one is aromatic and which form ortho- or ortho- and pericondensed ring systems.

The remainder or residue A may be substituted by one or more substituents on the aromatic ring member.

Exemplary substituents R are indicated below, but these are not limiting. Any substituent can be present on the cyclic ring member, providing that it does not interfere (i.e., is "inert") with the desired final product.

Since the remainder or residue A may comprise several alkoxy radicals, among others, the process of the invention is well suited to acylate polyalkoxylated compounds.

The process of the invention is particularly well suited for the acylation of aromatic ethers/phenols having the formula (Ia):

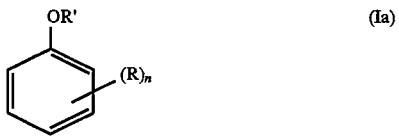

wherein n is a number less than or equal to 4, preferably 0, 1 or 2; the radical R' is a hydrogen atom or a linear or branched alkyl radical having from 1 to 6 carbon atoms, preferably 1 to 4 carbon atoms, such as methyl, ethyl, propyl, isopropyl, butyl, isobutyl, sec-butyl, tert-butyl, or phenyl; and the radicals R, which may be identical or different, are each a hydrogen atom, a linear or branched alkyl radical having from 1 to 6 carbon atoms, preferably 1 to 4 carbon atoms, such as methyl, ethyl, propyl, isopropyl, butyl, isobutyl, sec-butyl or tert-butyl, a linear or branched alkoxy radical having from 1 to 6 carbon atoms, preferably 1 to 4 carbon atoms, such as methoxy, ethoxy, propoxy, isopropoxy, butoxy, isobutoxy, sec-butoxy or tert-butoxy, a hydroxy group, a halogen atom, preferably a fluorine, chlorine or bromine atom, with the proviso that the radicals R' and R and the two successive atoms of the benzene ring may together form a cyclic ring member containing 5 to 7 atoms, optionally also comprising an additional heteroatom.

When n is greater than or equal to 1, the radicals R' and R and the two successive atoms of the benzene ring may be bonded together by an alkylene, alkenylene or alkenylidene radical having from 2 to 4 carbon atoms, to form a saturated, unsaturated or aromatic heterocycle having from 5 to 7 carbon atoms. One or more of the carbon atoms may be replaced by an additional heteroatom, preferably oxygen. Thus, the radicals R' and R can define a methylene dioxy or ethylene dioxy radical.

The process of the invention is more particularly applicable to aromatic ethers of formula (Ia) wherein n equals 1, and the radicals R and R' each represent alkoxy radicals, which may be identical or different.

Particularly exemplary compounds of formula (I) include phenolic compounds such as phenol, o-cresol and gaiacol; monoethers such as anisole, ethoxybenzene (phenetole), butoxybenzene, isobutoxybenzene, 2-chloroanisole, 3-chloroanisole, 2-bromoanisole, 3-bromoanisole, 2-methylanisole, 3-methylanisole, 2-ethylanisole, 3-ethylanisole, 2-isopropylanisole, 3-isopropylanisole, 2-propylanisole, 3-propylanisole, 2-allylanisole, 2-butylanisole, 3-butylanisole, 2-tert-butylanisole, 3-tert-butylanisole, 2-benzylanisole, 2-cyclohexylanisole, 1-bromo-2-ethoxybenzene, 1-bromo-3-ethoxybenzene, 1-chloro 2-ethoxybenzene, 1-chloro-3-ethoxybenzene, 1-ethoxy-2-ethylbenzene, 1-ethoxy-3-ethylbenzene, 2,3-dimethylanisole and 2,5-dimethylanisole; diethers such as veratrol, 1,3-dimethoxybenzene, 1,2-diethoxybenzene, 1,3-diethoxybenzene, 1,2-dipropoxybenzene, 1,3-dipropoxybenzene, 1,2-methylenedioxybenzene and 1,2-ethylenedioxybenzene; and triethers such as 1,2,3-trimethoxybenzene, 1,3,5-trimethoxybenzene and 1,3,5-triethoxybenzene.

Phenol, anisole and veratrol are the particularly preferred.

The acylation reactant has the following formula (II), in particular:

wherein $R_1$ is a linear or branched, saturated or unsaturated aliphatic radical having from 1 to 24 carbon atoms; a monocyclic or polycyclic, saturated, unsaturated or aromatic cycloaliphatic radical having from 4 to 8 carbon atoms; or a linear or branched, saturated or unsaturated aliphatic radical which comprises a cyclic substituent; and X' is a halogen atom, preferably a chlorine or bromine atom, or a —O—CO—$R_2$ radical, in which $R_2$, which may be identical to or different from $R_1$, has the same definition as $R_1$.

The term "cyclic substituent" is defined above.

More preferably, $R_1$ is a linear or branched alkyl radical having from 1 to 12 carbon atoms, preferably 1 to 6 carbon atoms: the hydrocarbon chain or backbone can be interrupted by a heteroatom (oxygen, for example), by a functional group (CO—, for example) and/or bear at least one substituent (a halogen or $CF_3$ group, for example).

$R_1$ is preferably an alkyl radical having from 1 to 4 carbon atoms, such as methyl, ethyl, propyl, isopropyl, butyl, isobutyl, sec-butyl and tert-butyl radicals.

Also, preferably, the radical $R_1$ is a phenyl radical which can be substituted. Any substituent can be present on the cyclic ring member provided that it does not interfere with the desired product.

Particularly exemplary such substituents include a linear or branched alkyl radical having from 1 to 6 carbon atoms, preferably 1 to 4 carbon atoms, such as methyl, ethyl, propyl, isopropyl, butyl, isobutyl, sec-butyl and tert-butyl radicals; a linear or branched alkoxy radical having from 1 to 6 carbon atoms, preferably 1 to 4 carbon atoms, such as methoxy, ethoxy, propoxy, isopropoxy, butoxy, isobutoxy, sec-butoxy and tert-butoxy radicals; a hydroxyl group; or a halogen atom, preferably a fluorine, chlorine or bromine atom.

Acylation or acylating agents of formula (II) which are preferred are those in which X in a chlorine atom and $R_1$ is a methyl or ethyl radical.

When the acylation agent is an acid anhydride, the preferred compounds of formula (II) are those in which $R_1$ and $R_2$ are identical and are each an alkyl radical having from 1 to 4 carbon atoms.

Particularly exemplary acylation agents of formula (II) include:

Acetyl chloride,
Propanoyl chloride,
Isobutanoyl chloride,
Pivaloyl chloride,
Acetic anhydride,
Isobutyric anhydride,
Trifluoroacetic anhydride.

In accordance with the process of the invention, acylation of an aromatic compound is carried out in the presence of a catalyst selected from among the bismuth halides, or any precursor compound which can generate a bismuth halide in situ.

The preferred compounds are bismuth halides, preferably the chloride, bromide or iodide, more preferably bismuth chloride $BiCl_3$, bismuth bromide $BiBr_3$, and bismuth iodide $BiI_3$.

Any bismuth compound can be used, provided that it is associated with a halogen source.

Thus, metallic bismuth can be used, or any inorganic or organic bismuth derivative. The moiety associated with the bismuth is not critical.

Exemplary catalysts which are well suited for the process of the present invention include bismuth oxides; bismuth hydroxides; the salts of inorganic hydrogen acids such as bismuth sulfide, selenide or telluride; the salts of inorganic oxyacids such as bismuth sulfite, sulfate, nitrite, nitrate, phosphite, phosphate, pyrophosphate, carbonate, perchlorate, antimonate, arsenate, selenite, selenate; the salts of oxyacids derived from transition metals such as bismuth vanadate, niobate, tantalate, chromate, molybdate, tungstate and permanganate, and the oxides of bismuth and germanium.

Salts of aliphatic or aromatic organic acids are also suitable, such as bismuth acetate, propionate, benzoate, salicylate, oxalate, tartrate, lactate and citrate; and phenates such as bismuth gallate and pyrogallate. These salts and phenates can also be in the form of bismuthyl salts.

Other inorganic or organic such compounds include binary combinations of bismuth with elements such as phosphorus and arsenic; heteropolyacids containing bismuth and salts thereof. Aliphatic and aromatic bismuthines are also suitable.

Particularly exemplary thereof are:

(i) oxides: $BiO$, $Bi_2O_3$, $Bi_2O_4$, $Bi_2O_5$;

(ii) hydroxides: $Bi(OH)_3$;

(iii) salts of inorganic hydrogen acids: bismuth sulfide $Bi_2S_3$, bismuth selenide $Bi_2Se_3$, bismuth telluride $Bi_2Te_3$;

(iv) salts of inorganic oxyacids: basic bismuth sulfite $Bi_2(SO_3)_3$, $Bi_2O_3.5H_2O$, neutral bismuth sulfate $Bi_2(SO_4)_3$, bismuthyl sulfate $(BiO)HSO_4$, bismuthyl nitrite $(BiO)NO_2.0.5H_2O$, neutral bismuth nitrate $Bi(NO_3)_3$ $5H_2O$, the double nitrate of bismuth and magnesium $2Bi(NO_3)_3$, $3Mg(NO_3)_2.24H_2O$ bismuthyl nitrate $(BiO)NO_3$, bismuth phosphite $Bi_2(PO_3H)_3.3H_2O$, neutral bismuth phosphate $BiPO_4$, bismuth pyrophosphate $Bi_4(P_2O_7)_3$, bismuthyl carbonate $(BiO)_2CO_3.0.5H_2O$, neutral bismuth perchlorate $Bi(ClO_4)_3.5H_2O$, bismuthyl perchlorate $(BiO)$ $ClO_4$, bismuth antimonate $BiSbO_4$, neutral bismuth arsenate $Bi(AsO_4)_3$, bismuthyl arsenate $(BiO)AsO_4.5H_2O$, bismuth selenite $Bi_2(SeO_3)_3$;

(v) salts of oxyacids derived from transition metals: bismuth vanadate $BiVO_4$, bismuth niobate $BiNbO_4$, bismuth tantalate $BiTaO_4$, neutral bismuth chromate $Bi_2(CrO_4).3.5H_2O$, bismuthyl dichromate $(BiO)_2Cr_2O_7$, acidic bismuthyl chromate $H(BiO)CrO_4$, the double chromate of bismuthyl and potassium $K(BiO)Cr_3O_{10}$, bismuth molybdate $Bi_2(MoO_4)_3$, bismuth tungstate $Bi_2(WO_4)_3$, the double molybdate of bismuth and sodium $NaBi(MoO_4)_2$, basic bismuth permanganate $Bi_2O_2(OH)MnO_4$, the oxide of bismuth and germanium $Bi_{12}GeO_{20}$;

(vi) salts of organic aliphatic or aromatic acids: bismuth acetate $Bi(C_2H_3O_2)_3$, bismuthyl propionate $(BiO)C_3H_5O_2$, basic bismuth benzoate $C_6H_5CO_2Bi(OH)_2$, bismuthyl salicylate $C_6H_4CO_2(BiO)(OH)$, bismuth oxalate $(C_2O_4)_3Bi_2$, bismuth tartrate $Bi_2(C_4H_4O_6)_3.6H_2O$, bismuth lactate $(C_6H_9O_5)OBi, 7H_2O$, bismuth citrate $C_6H_5O_7Bi$;

(vii) phenates: basic bismuth gallate $C_7H_7O_7Bi$, basic bismuth pyrogallate $C_6H_3(OH)_2(OBi)(OH)$.

Other inorganic or organic compounds are also suitable, i.e., bismuth phosphide $BiP$, bismuth arsenide $Bi_3As_4$, sodium bismuthate $NaBiO_3$, bismuth/thiocyanic acids $H_2[Bi(BNS)_5]$, $H_3[Bi(BNS)_6]$ and the potassium and sodium salts thereof, trimethylbismuthine $Bi(CH_3)_3$, and triphenylbismuthine $Bi(C_6H_5)_3$.

The following are preferred bismuth derivatives for carrying out the process of the invention: bismuth oxides, bismuth hydroxides, the bismuth or bismuthyl salts of inorganic hydrogen acids, the bismuth or bismuthyl salts of inorganic oxyacids, the bismuth or bismuthyl salts of organic aliphatic or aromatic acids, and the bismuth or bismuthyl phenates.

A particularly preferred category of catalysts for carrying out the process of the invention comprises bismuth oxides $Bi_2O_3$ and $Bi_2O_4$, bismuth hydroxide $Bi(OH)_3$, neutral bismuth sulfate $Bi_2(SO_4)_3$, bismuth chloride $BiCl_3$, bismuth bromide $BiBr_3$, bismuth iodide $BiI_3$, neutral bismuth nitrate $Bi(NO_3)_3.5H_2O$, bismuthyl nitrate $BiO(NO_3)$, bismuthyl carbonate $(BiO)_2CO_3.0.5H_2O$, bismuth acetate $Bi(C_2H_3O_2)_3$, and bismuth salicylate $C_6H_4CO_2(BiO)(OH)$.

In respect of the halogen source, any compound can be used which comprises halogen ions to generate the bismuth halide in situ.

Exemplary halogen sources include the molecular halogens, any halide of an inorganic or organic acid, in particular of an aliphatic carboxylic acid, and any inorganic or organic metallic or metalloidal salt which can generate a halogenated species of bismuth.

More particularly exemplary thereof are chlorine or bromine, hydrochloric acid, hydrobromic acid, acetyl chloride, silicon chloride $SiCl_4$, halogenosilanes such as $Me_3SiCl$, $Me_2SiCl_2$, $MeSiCl_3$, $PhMe_2SiCl$, phosphorous chloride $PCl_3$, and sulfur chloride $SCl_2$.

In a preferred embodiment of the process of the invention, the subject reaction is carried out in an organic solvent.

Preferably, a solvent for the starting material is used.

Particularly exemplary solvents include aliphatic or aromatic hydrocarbons, which either may or may not be halogenated, and aliphatic, cycloaliphatic or aromatic ether/oxides.

Exemplary aliphatic hydrocarbons include paraffins such as hexane, heptane, octane, nonane, decane, undecane, dodecane, tetradecane or cyclohexane, and naphthalene and aromatic hydrocarbons, more particularly aromatic hydrocarbons such as benzene, toluene, xylenes, cumene, and petroleum cuts constituted by a mixture of alkylbenzenes, in particular Solvesso® type cuts.

Exemplary halogenated aliphatic or aromatic hydrocarbons include perchlorinated hydrocarbons such as tetrachloromethane, tetrachloroethylene, and hexachloroethane; partially chlorinated hydrocarbons such as dichloromethane, chloroform, 1,2-dichloroethane, 1,1,1-trichloroethane, 1,1,2,2-tetrachloroethane, pentachloroethane, trichloroethylene, 1-chlorobutane, and 1,2-dichlorobenzene; monochlorobenzene, 1,2-dichlorobenzene, 1,3-dichlorobenzene, 1,4-dichlorobenzene, 1,2,4-trichlorobenzene or mixtures of different chlorobenzenes; bromoform, bromoethane or 1,2-dibromoethane; monobromobenzene or mixtures of monobromobenzene with one or more dibromobenzenes; and 1-bromonaphthalene.

Aliphatic, cycloaliphatic or aromatic organic ether/oxides can also be used as organic solvents, in particular diethyl oxide, dipropyl oxide, diisopropyl oxide, dibutyl oxide, methyltertiobutyl ether, dipentyl oxide, diisopentyl oxide, the dimethylether of ethyleneglycol (1,2-dimethoxyethane), the dimethylether of diethyleneglycol (1,5-dimethoxy 3-oxapentane); biphenyl or benzyl oxide; dioxane, or tetrahydrofuran (THF).

The preferred solvents are dichloromethane, tetrachloromethane, THF and diethyl oxide.

Mixtures of organic solvents can also be used.

Preferably, the starting material substrate is used as the reaction solvent.

The solvent is preferably anhydrous.

In a first step of the process of the invention, acylation of the aromatic ether/phenol is carried out. In a subsequent step, the reaction mass obtained is hydrolyzed.

The ratio between the number of moles of aromatic compound and the number of moles of acylation agent can vary since the substrate can serve as the reaction solvent. Thus, this ratio advantageously ranges from 0.1 to 10, and preferably is about 4.0.

The amount of catalyst used is determined such that the ratio between the number of moles of catalyst and the number of moles of acylation agent is characteristically less than 1.0, preferably ranging from 0.001 to 0.8, more preferably from 0.02 to 0.2.

The amount of organic solvent is generally selected such that the ratio between the number of moles of organic solvent and the number of moles of aromatic compound preferably ranges from 0 to 100, more preferably from 0 to 50.

The temperature at which the acylation reaction is carried out depends on the reactivity of the starting substrate and that of the acylation agent.

It advantageously ranges from 20° C. to 200° C., preferably from 40° C. to 150° C.

The reaction is generally carried out at atmospheric pressure, but higher or lower pressures may also be suitable.

From a practical standpoint, there are no constraints regarding the use of the reactants. They can be introduced in any order.

After intimately contacting the reactants, the reaction mixture is heated to the desired temperature.

In another embodiment of the process of the invention, one of the reactants (acylation agent or aromatic compound) is heated with the catalyst and then the other reactant is introduced.

The reaction time is a function of several parameters. Typically, it ranges from 30 minutes to 8 hours.

In a downstream step of the process of the invention, the reaction mass obtained is hydrolyzed.

The amount of water employed can vary very widely. The ratio between the number of moles of water and the number of moles of aromatic compound advantageously ranges from 10 to 100, preferably from 20 to 30.

In a preferred embodiment of the invention, this operation entails adding the reaction medium to a water base at a temperature ranging between 0° C. to 100° C., preferably from 15° C. to 30° C.

In another embodiment, the water is replaced by a basic aqueous solution, typically caustic soda, sodium carbonate or sodium bicarbonate, at a concentration of from 5% to 20% by weight.

The catalyst is preferably separated from the reaction medium by filtering. The catalyst can be recycled after drying.

At the end of the reaction, the desired product, namely, the hydroxy- and/or alkoxyaromatic alkylketone, is recovered in the organic phase.

The aqueous and organic phases are separated.

The organic phase is washed several times with water, preferably twice.

The aqueous and organic phases are separated.

The hydroxy- and/or alkoxyaromatic alkylketone is recovered from the organic phase via any known technique by elimination of the organic solvent, by distillation or by crystallization.

The process of the invention is particularly well suited for the preparation of 4-methoxyacetophenone and 3,4-dimethoxyacetophenone, commonly referred to as acetoveratrol, by acetylation of anisole or veratrol, respectively.

One essential feature of the process of the invention is a catalytically effective amount of a bismuth catalyst.

One advantage of the process of the invention is that the acylation reaction is carried out in the absence of O-demethylation of the veratrol.

Further, only a minor amount of the ortho isomer is formed, due to the para-directing nature of the catalyst.

In order to further illustrate the present invention and the advantages thereof, the following specific examples are given, it being understood that same are intended only as illustrative and in nowise limitative.

In said examples, the yields indicated have the following definitions:

$$\text{Yield: } RR_{E.A.} = \frac{\text{number of moles of aromatic ether introduced, \%}}{\text{number of moles of aromatic alkoxy alkylacetone formed}}$$

$$\text{Yield: } RR_{A.A.} = \frac{\text{number of moles of acylation agent introduced, \%}}{\text{number of moles of aromatic alkoxy alkylacetone formed}}$$

EXAMPLES 1 TO 10

The following reagents were charged into a 25 ml reactor provided with a coolant, a thermometer and a magnetic stirrer:

(i) 10.8 g of anisole, (ii) 9.42 of acetyl chloride, (iii) 10 ml of a solvent, the nature of which is indicated in the following Table I, (iv) x molar % with respect to the anisole, of a catalyst, the nature of which is also indicated in the following Table I.

The reaction medium was refluxed for the period of time indicated in Table I.

At the end of the reaction, a portion of the reaction medium was removed and hydrolyzed with a 10% aqueous solution of sodium carbonate.

The organic phase was separated from the aqueous phase, the solvent was evaporated off and the products were analyzed by means of NMR.

The 4-methoxyacetophenone yields are expressed with respect to the anisole introduced.

TABLE I

| Example No. | Nature of catalyst | Mole % of catalyst with respect to anisole | Nature of solvent (volume ratio) | Time (h) | Yield $RR_{B.A.}$ (%) |
| --- | --- | --- | --- | --- | --- |
| 1 | $BiCl_3$ | 5 | Dichloromethane Ethyl ether (10/1) | 3 | 28 |
| 2 | $BiCl_3$ | 15 | Dichloromethane Ethyl ether (10/1) | 3 | 55 |
| 3 | $BiCl_3$ | 5 | Dichloromethane | 8 | 40 |
| 4 | $BiCl_3$ | 5 | Dichloromethane Ethyl ether (10/1) | 8 | 33 |
| 5 | $BiCl_3$ | 15 | Dichloromethane Ethyl ether (10/1) | 4 | 47 |
| 6 | $BiCl_3$ | 5 | Tetrachloromethane | 4 | 18 |
| 7 | $BiCl_3$ | 5 | Dichloromethane THF (10/1) | 3 | 19 |
| 8 | BiOCl | 5 | Dichloromethane Ethyl ether (10/1) | 4 | 23 |
| 9 | $Bi_2O_3$ | 5 | Dichloromethane Ethyl ether (10/1) | 3 | 55 |
| 10 | $Bi_2O_3$ | 10 | Dichloromethane Ethyl ether (10/1) | 2 | 60 |

EXAMPLE 11

The procedure of Examples 1 to 10 was repeated, except that the reaction was carried out at room temperature.

The results obtained were as follows:

TABLE II

| Example No. | Nature of catalyst | Mole % of catalyst with respect to anisole | Nature of solvent (volume ratio) | Time (h) | Yield $RR_{B.A.}$ (%) |
| --- | --- | --- | --- | --- | --- |
| 11 | $BiCl_3$ | 5 | Dichloromethane Ethyl ether (10/1) | 120 | 5 |

EXAMPLES 12 TO 16

The procedure of Examples 1 to 10 was repeated, except that the nature of the acylation agent was changed as indicated in the following Table III:

TABLE III

| Example No. | Nature of catalyst | Mole % of catalyst with respect to anisole | Nature of solvent (volume ratio) | Nature of acylation agent | Time (h) | Yield $RR_{B.A.}$ (%) |
| --- | --- | --- | --- | --- | --- | --- |
| 12 | $BiCl_3$ | 10 | Benzene | Isobutanoyl chloride | 3 | 62 |
| 13 | $Bi_2O_3$ | 5 | Dichloromethane Ethyl ether (10/1) | Isobutanoyl chloride | 5 | 69 |
| 14 | $Bi_2O_3$ | 5 | Benzene | Isobutanoyl chloride | 4 | 68 |
| 15 | $Bi_2O_3$ | 5 | Dichloromethane Ethyl ether (10/1) | Pivaloyl chloride | 4 | 70 |
| 16 | $BiCl_3$ | 10 | Dichloromethane Ethyl ether (10/1) | Acetic anhydride | 4 | 8 |

EXAMPLES 17 TO 19

The following reagents were charged into a 25 ml reactor provided with a coolant, a thermometer and a magnetic stirrer:

(i) 1.08 (0.01 mole) of anisole, (ii) 2.2 g (0.028 mole) of acetyl chloride, (iii) x molar % with respect to the anisole, of a catalyst, the nature of which is indicated in the following Table IV.

The reaction mixture was refluxed for the period of time indicated in Table IV.

At the end of the reaction, 30 ml of an aqueous 5% caustic soda solution were added.

After treatment as described in Example 1, the organic products were analyzed by means of NMR.

The 4-methoxyacetophenone yields are expressed with respect to the anisole introduced.

In certain examples, the nature of the aromatic substrate and the acylation agent was changed.

The following reagents were charged into a 25 ml reactor provided with a coolant, a thermometer and a magnetic stirrer:

(i) 40 mmole of an aromatic substrate, (ii) 10 mmole of acylation agent, (iii) x molar % with respect to the acylation agent, of a catalyst, the nature of which is indicated in the following Table V.

The reaction mixture was refluxed at the temperature and for the period of time indicated in Table V.

At the end of the reaction, 20 ml of an aqueous 5% caustic soda solution were added.

After treatment as described in Example 1, the organic products were analyzed by means of NMR.

The aromatic ketone yields are expressed with respect to the acylation agent employed.

TABLE V

| Example No. | Nature of aromatic substrate | Nature of catalyst | Mole % of catalyst with respect to anisole | Nature of acylation agent | Temperature (°C.) | Time (h) | Yield $RR_{B.A.}$ (%) |
|---|---|---|---|---|---|---|---|
| 20 | Anisole | $BiCl_3$ | 10 | Acetyl chloride | 50 | 1 | 60 |
| 21 | Anisole | $BiCl_3$ | 5 | Isobutanoyl chloride | 70 | 2 | 80 |
| 22 | Anisole | $BiCl_3$ | 10 | Pivaloyl chloride | reflux | 3 | 95 |
| 23 | Anisole | $BiCl_3$ | 10 | Benzoyl chloride | 85 | 6 | 100 |
| 24 | Veratrol | $BiCl_3$ | 10 | Acetyl chloride | 50 | 1 | 80 |
| 25 | Veratrol | $BiCl_3$ | 10 | Isobutanoyl chloride | 70 | 2 | 82 |
| 26 | Anisole | $BiCl_3$ | 10 | Acetic anhydride | reflux | 6.5 | 87 |
| 27 | Anisole | $BiCl_3$ | 10 | Isobutyric anhydride | reflux | 6 | 67 |
| 28 | Anisole | $BiCl_3$ | 10 | Acetic anhydride | reflux | 3.5 | 100 |
| 29 | Anisole | $BiCl_3$ | 10 | Isobutyric anhydride | reflux | 6 | 65 |
| 30 | Veratrol | $BiCl_3$ | 10 | Acetic anhydride | reflux | 7.5 | 65 |
| 31 | Veratrol | $BiCl_3$ | 10 | Isobutyric anhydride | reflux | 7 | 24 |

TABLE IV

| Example No. | Nature of catalyst | Mole % of catalyst with respect to anisole | Nature of acylation agent | Time (min) | Yield $RR_{B.A.}$ (%) |
|---|---|---|---|---|---|
| 17 | $BiCl_3$ | 5 | Acetyl chloride | 45 | 43 |
| 18 | $BiCl_3$ | 15 | Acetyl chloride | 30 | 37 |
| 19 | $Bi_2O_3$ | 5 | Acetyl chloride | 90 | 69 |

EXAMPLES 20 TO 31

In the following examples, an excess of aromatic substrate was used.

EXAMPLE 32

The following reagents were charged into a 100 ml reactor provided with a coolant, a thermometer and a magnetic stirrer:

(i) 43.2 g (0.4 mole) of anisole, (ii) 10.6 (10 mmole) of isobutanoyl chloride, (iii) 3.15 g (1 mmole) of bismuth chloride.

The reaction mixture was heated to 85° C. using a paraffin heating bath for a time period of 6 hours.

At the end of the reaction, after cooling, the reaction medium was hydrolyzed by adding thereto 100 ml of an aqueous 1.25N caustic soda solution.

The catalyst was removed by filtering, following decanting; the aqueous phase was extracted with 100 ml of ether.

The organic phases were dried over sodium sulfate, filtered, and then concentrated.

3 g of the organic phase were removed and analyzed using a Silicagel Merek 60 chromatographic column. Elution with pentane extracted the anisole; the desired ketone was eluted with ethyl ether.

The yield of 4-methoxyacetophenone was 87% with respect to the isobutanoyl chloride.

EXAMPLES 33 TO 44

These examples reflect the influence of the nature and amount of catalyst used.

The conditions of the preceding example were reproduced.

The differing reaction times are indicated in the following Table VI.

The aromatic substrate was anisole in all of the examples. The excess anisole served as a reaction solvent.

TABLE VI

| Example No. | Nature of catalyst | Mole % of catalyst with respect to acylation agent | Time (h) | Yield $RR_{A.A.}$ (%) |
|---|---|---|---|---|
| 32 | $BiCl_3$ | 10 | 6 | 87 |
| 33 | $BiCl_3$ | 1 | 6.5 | 40 |
| 34 | $Bi_2O_3$ | 5 | 4 | 74 |
| 35 | $Bi_2O_3$ | 0.5 | 4 | 35 |
| 36 | $Bi_{12}GeO_{20}$ | 1 | 2 | 52 |
| 37 | $2Bi_2O_3,3ZnO_2$ | 2.5 | 3.5 | 53 |
| 38 | $(CH_3COO)_3Bi$ | 10 | 3 | 49 |
| 39 | $(BiO)_2CO_3$ | 10 | 6 | 48 |
| 40 | $BiI_3$ | 10 | 6 | 11.5 |
| 41 | $BiBr_3$ | 10 | 6 | 54 |
| 42 | $C_6H_4CO_2(BiO)(OH)$ | 10 | 6.5 | 51 |
| 43 | $BiOCl$ | 10 | 6 | 45 |
| 44 | $Ph_3Bi$ | 10 | 6.5 | 62 |

EXAMPLE 45

The following reagents were charged into a 100 ml reactor provided with a coolant, a thermometer and a magnetic stirrer:

(i) 55.2 g (0.4 mole) of veratrol, (ii) 10.6 (10 mmole) of isobutanoyl chloride, (iii) 3.15 g (1 mmole) of bismuth chloride.

The reaction mixture was heated to 85° C. using a paraffin heating bath for a time period of 6 hours.

At the end of the reaction, after cooling, the reaction medium was hydrolyzed by adding thereto 100 ml of an aqueous 1.25N caustic soda solution.

The catalyst was removed by filtering, following decanting; the aqueous phase was extracted with 100 ml of ether.

The organic phases were dried over sodium sulfate, filtered, and then concentrated.

3 g of the organic phase were distilled. 3,4-Dimethoxyisobutyrophenone was recovered at 118° C. at 0.1 mm of mercury.

The yield of 3,4-dimethoxyisobutyrophenone was with respect to the isobutanoyl chloride.

EXAMPLE 46 AND 47

These examples reflect the influence of the nature and amount of catalyst used.

The conditions of the preceding example were reproduced.

The differing reaction times are indicated in the following Table VII.

The aromatic substrate was veratrol in all of the examples. The excess veratrol served as a reaction solvent.

TABLE VII

| Example No. | Nature of catalyst | Mole % of catalyst with respect to acylation agent | Time (h) | Yield $RR_{A.A.}$ (%) |
|---|---|---|---|---|
| 46 | $BiCl_3$ | 10 | 6.5 | 88 |
| 47 | $Bi_2O_3$ | 5 | 4 | 58 |

EXAMPLES 48 TO 53 (Comparative)

The nature of the catalyst was changed to other metallic catalysts in these examples.

The conditions of above Example 32 were otherwise repeated.

The aromatic substrate was anisole in all of the examples. The excess anisole served as a reaction solvent.

TABLE VIII

| Example No. | Nature of catalyst | Mole % of catalyst with respect to acylation agent | Time (h) | Yield $RR_{A.A.}$ (%) |
|---|---|---|---|---|
| 32 | $BiCl_3$ | 10 | 6 | 87 |
| 48 | $SbCl_3$ | 10 | 6 | 27 |
| 49 | $ZnCl_2$ | 5 | 6 | 46 |
| 50 | $FeCl_3$ | 5 | 6 | 58 |
| 51 | $Sb_2O_3$ | 5 | 4 | 20 |
| 52 | $Fe_2O_3$ | 5 | 6.5 | 5 |
| 53 | $ZnO$ | 5 | 6.5 | 60 |

EXAMPLE 54

The following reagents were charged into a 100 ml reactor provided with a coolant, a thermometer and a magnetic stirrer:

(i) 43.2 g (0.4 mole) of anisole, (ii) 10.6 (10 mmole) of hexanoyl chloride, (iii) 3.15 g (1 mmole) of bismuth chloride.

The reaction mixture was heated to 85° C. using a paraffin heating bath for a time period of 6 hours.

Every two hours, 10.6 g (10 mmole) of hexanoyl chloride were added.

After six hours of heating, corresponding to a total introduction of 40 mmole of hexanoyl chloride, the reaction medium was cooled.

The reaction medium was hydrolyzed by adding thereto 100 ml of an aqueous 1.25N caustic soda solution.

The catalyst was removed by filtering, following decanting; the aqueous phase was extracted with 100 ml of ether.

The organic phases were dried over sodium sulfate, filtered, and then concentrated.

3 g of the organic phase were withdrawn and analyzed via chromatography on a Silicagel Merek 60 column. Elution with pentane extracted the anisole; the desired ketone was eluted with ethyl ether.

The yield of pentylpentylketone was 55% with respect to the hexanoyl chloride.

EXAMPLE 55

The conditions of this example were those of Example 34; the catalyst was removed by filtration and recycled and re-used under the same conditions as those of Example 34.

The catalyst introduced had a 74% bismuth content which, taking account of the masses employed, represented 96% of the bismuth used in Example 34.

A yield of 47% of 4-methoxyisobutyrophenone was obtained, evidencing that the catalyst was still active.

EXAMPLE 56

This example evidences that the catalyst did not degrade the final product obtained.

The following reagents were charged into a 50 ml reactor:

(i) 5 g of 4-methoxyacetophenone, (ii) 2.1 g of bismuth trichloride.

The reaction mixture was heated to 150° C. for two hours.

After cooling, the reaction mass was hydrolyzed with 100 ml of an aqueous 1.25N caustic soda solution.

The aqueous phase was extracted with ether.

The organic phase was dried over sodium sulfate, filtered and concentrated.

The NMR spectrum evidenced that the 4-methoxyacetophenone had not degraded.

EXAMPLES 57 TO 61

These examples demonstrated the role of the halides in the medium of reaction.

The following reagents were charged into a 25 ml reactor provided with a coolant, a thermometer and a magnetic stirrer:

(i) 1.08 (0.01 mole) of anisole, (ii) 2.55 g (0.025 mole) of acetic anhydride, (iii) x mole %, expressed with respect to the acylation agent, of a catalyst, the nature of which is indicated in the following Table IX.

The reaction mixture was heated to 80° C. using a paraffin heating bath for a time period which is also indicated in Table IX.

At the end of the reaction, 20 ml of an aqueous 5% caustic soda solution were added; the catalyst was removed by filtering, following decanting; the aqueous phase was extracted with 20 ml of ether.

The organic phase was dried over sodium sulfate, filtered and concentrated.

The product was analyzed via NMR.

The yield of 4-methoxyacetophenone is expressed with respect to the acylation agent.

TABLE IX

| Example No. | Nature of catalyst | Mole % of catalyst with respect to acylation agent | Time (h) | Yield RR$_{AA}$ (%) |
|---|---|---|---|---|
| 57 | Bi$_2$O$_3$ | 10 | 4 | 0 |
| 58 | C$_6$H$_4$CO$_2$ (BiO) (OH) | 10 | 4.5 | 0 |
| 59 | Bi$_2$O$_3$,6CH$_3$COCl | 5 | 7 | 79 |
| 60 | Bi$_2$O$_3$,6Me$_3$SiCl | 5 | 7 | 39 |
| 61 | BiCl$_3$ | 10 | 6 | 100 |

EXAMPLE 62

This example compares the influence of the nature of the acid halide.

The operating procedure of Example 41 was repeated.

The following results were obtained:

TABLE X

| Example No. | Nature of catalyst | Nature of acylation agent | Mole % of catalyst with respect to acylation agent | Time (h) | Yield RR$_{AA}$ (%) |
|---|---|---|---|---|---|
| 41 | BiBr$_3$ | Isobutanoyl chloride | 10 | 6 | 54 |
| 61 | BiBr$_3$ | Acetyl bromide | 10 | 4 | 21 |

While the invention has been described in terms of various preferred embodiments, the skilled artisan will appreciate that various modifications, substitutions, omissions, and changes may be made without departing from the spirit thereof. Accordingly, it is intended that the scope of the present invention be limited solely by the scope of the following claims, including equivalents thereof.

What is claimed is:

1. A process for the acylation of an aromatic ether or phenol to produce a hydroxy- or alkoxyaromatic alkylketone, said process comprising reacting an aromatic ether or phenol with an acylation agent in the presence of a catalytically effective amount of a bismuth halide or an in situ precursor thereof at conditions effective to produce a hydroxy- or alkoxyaromatic alkylketone.

2. The process as defined by claim 1, said aromatic ether or phenol having the general formula (I):

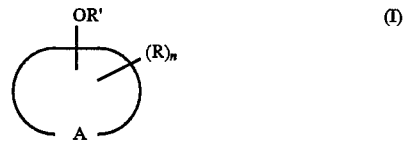

wherein A is the residue of a substituted or unsubstituted ring member defining at least a portion of a monocyclic or polycyclic carboxylic aromatic nucleus which comprises at least one OR' group; R is at least one inert substituent, which may be identical of different; R' is a hydrogen atom or a hydrocarbon radical having from 1 to 24 carbon atoms, which comprises a linear or branched, saturated or unsaturated acyclic aliphatic radical, a monocyclic or polycyclic, saturated, unsaturated or aromatic cycloaliphatic radical, or a linear or branched, saturated or unsaturated aliphatic radical substituted by a cyclic substituent; and n is a number less than or equal to 4.

3. The process as defined by claim 2, wherein formula (I), R' is a hydrogen atom or a substituted or unsubstituted linear or branched, saturated or unsaturated acyclic aliphatic radical, the hydrocarbon backbone of which optionally being interrupted by a heteroatom or a functional group; a linear or branched, saturated or unsaturated acyclic aliphatic radical which comprises a substituted or unsubstituted ring member; a substituted or unsubstituted saturated carbocyclic radical or a substituted or unsubstituted carbocyclic radical which comprises 1 or 2 sites of unsaturation in the ring member; or a substituted or unsubstituted aromatic carbocyclic radical.

4. The process as defined by claim 2, wherein formula (I), R' is a linear or branched alkyl radical having from 1 to 4 carbon atoms, or a phenyl radical.

5. The process as defined by claim 2, wherein formula (I), A is a substituted or unsubstituted residue of a monocyclic aromatic carbocyclic compound having at least 4 carbon atoms, or a substituted or unsubstituted residue of a polycyclic carbocyclic compound.

6. The process as defined by claim 1, said aromatic ether or phenol having the formula (Ia):

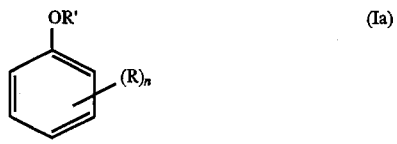

wherein n is 0, 1 or 2; R' is a hydrogen atom, or methyl, ethyl, propyl, isopropyl, butyl, isobutyl, sec-butyl, tert-butyl or phenyl; and R is a hydrogen atom, a linear or branched alkyl radical having from 1 to 6 carbon atoms, a linear or branched alkoxy radical having from 1 to 6 carbon atoms, fluorine, chlorine or bromine, with the proviso that R' and R and the two successive atoms of the aromatic ring may together form a cyclic ring member having from 5 to 7 atoms, optionally comprising an additional heteroatom.

7. The process as defined by claim 6, wherein formula (Ia), n is greater than or equal to 1, and R' and R and the two successive atoms of the aromatic ring are bonded together via an alkylene, alkenylene or alkenylidene radical having from 2 to 4 carbon atoms, to form a saturated, unsaturated or aromatic heterocycle having from 5 to 7 carbon atoms, with the proviso that one or more carbon atoms thereof can be replaced by a heteroatom.

8. The process as defined by claim 6, wherein formula (Ia), n equals 1; and R' and R are each an alkoxy radical, which may be identical or different.

9. The process as defined by claim 1, said aromatic ether or phenol comprising phenol, anisole or veratrol.

10. The process as defined by claim 1, said acylation agent having the formula (II):

wherein $R_1$ is a linear or branched, saturated or unsaturated aliphatic radical having from 1 to 24 carbon atoms; a monocyclic or polycyclic, saturated, unsaturated or aromatic cycloaliphatic radical having from 4 to 8 carbon atoms; or a linear or branched, saturated or unsaturated aliphatic radical substituted by a cyclic substituent; X' is a halogen atom, or an —O—CO—$R_2$ radical, in which $R_2$ which may be identical to or different from $R_1$, has the same definition as $R_1$.

11. The process as defined by claim 10, wherein formula (II), X is a chlorine atom and $R_1$ is a substituted or unsubstituted linear or branched alkyl radical having from 1 to 12 carbon atoms, the hydrocarbon backbone of which chain may be interrupted by a heteroatom or by a functional group.

12. The process as defined by claim 10, said acylation agent comprising acetyl chloride, propanoyl chloride, isobutanoyl chloride, pivaloyl chloride, acetic anhydride, isobutyric anhydride, or trifluoroacetic anhydride.

13. The process as defined by claim 1, carried out in the presence of bismuth chloride, bromide or iodide.

14. The process as defined by claim 1, carried out in the presence of a bismuth oxide, bismuth hydroxide, a bismuth or bismuthyl salt of an inorganic hydrogen acid, a bismuth or bismuthyl salt of an inorganic oxyacid, a salt of an oxyacid derived from a transition metal, a bismuth or bismuthyl salt of an organic aliphatic or aromatic acid, or a bismuth or bismuthyl phenate.

15. The process as defined by claim 14, carried out in the presence of molecular halogen, a halide of an organic aliphatic or aromatic acid, or a metallic or metalloidal salt, inorganic or organic, which can generate a halogenated form of bismuth.

16. The process as defined by claim 15, carried out in the presence of chlorine, bromine, hydrochloric acid, hydrobromic acid, acetyl chloride, silicon chloride $SiCl_4$, a halogenosilane, phosphorous chloride $PCl_3$, or sulfur chloride $SCl_2$.

17. The process as defined by claim 1, carried out in a reaction solvent which comprises the aromatic substrate, or an apolar, aprotic and slightly basic organic solvent.

18. The process as defined by claim 17, carried out in an organic solvent which comprises an aliphatic and/or aromatic hydrocarbon, optionally halogenated, or an aliphatic, cycloaliphatic or aromatic ether/oxide.

19. The process as defined by claim 18, said organic solvent comprising dichloromethane, tetrachloromethane, THF or diethyl oxide.

20. The process as defined by claim 1, wherein the ratio between the number of moles of aromatic compound and the number of moles of acylation agent ranges from 0.1 to 10.

21. The process as defined by claim 1, wherein the amount of catalyst is such that the ratio between the number of moles of catalyst and the number of moles of acylation agent is less than 1.0.

22. The process as defined by claim 1, carried out at a temperature ranging from 20° C. to 200° C.

* * * * *